United States Patent [19]
Wright

[11] Patent Number: 6,008,361
[45] Date of Patent: Dec. 28, 1999

[54] SUBSTITUTED PYRIDINES

[75] Inventor: Steven W. Wright, Old Lyme, Conn.

[73] Assignee: Pfizer Inc., New York, N.Y.

[21] Appl. No.: 09/196,728

[22] Filed: Nov. 20, 1998

Related U.S. Application Data

[62] Division of application No. 08/968,129, Nov. 12, 1997, abandoned.

[60] Provisional application No. 60/030,802, Nov. 14, 1996, abandoned.

[51] Int. Cl.[6] .................................................. C07D 213/40
[52] U.S. Cl. .......................... 546/307; 546/308; 546/309; 546/312
[58] Field of Search .................................. 546/307, 308, 546/309, 312

[56] References Cited

U.S. PATENT DOCUMENTS

| | | | |
|---|---|---|---|
| 3,822,276 | 7/1974 | Meisels et al. | 546/305 |
| 4,358,455 | 11/1982 | Atkinson et al. | 546/294 |
| 5,019,578 | 5/1991 | Fisher et al. | 514/275 |
| 5,059,602 | 10/1991 | Effland et al. | 514/258 |
| 5,627,200 | 5/1997 | Kreutter et al. | 514/367 |

FOREIGN PATENT DOCUMENTS

| | | |
|---|---|---|
| 435222 | 7/1991 | European Pat. Off. . |
| 0801060 | 10/1997 | European Pat. Off. . |
| 8003163 | 1/1996 | Japan . |
| 484135 | 2/1970 | Switzerland . |
| 9429290 | 12/1994 | WIPO . |
| 9635671 | 11/1996 | WIPO . |

OTHER PUBLICATIONS

Acheson, R. M., *The Chemistry of Heterocyclic Compounds,* 1960, p. 167.

Andersson, C–M., et al. "Regiochemistry of Palladium–Catalyzed Arylation Reations of Enol Ethers. Electronic Control of Selection for α–or β–Arylation," *J. Org. Chem.,* 1987, vol.52, pp. 3529–3536.

Barraclough, Paul et al. "Inotropic 'A' Ring Substituted Sulmazole and Isomazole Analogs." (Dep. Med. Chem., Wellcome Res. Lab., Beckenham/Kent, BR3 3BS, UK), *J. Med. Chem.,* 1990, 33 (8), pp. 2231–9.

Cooper, G. H. et al. (Chem. Def. Est., Porton Down/Salisbury, Engl.), *J. Chem. Soc.,* 1971, C (19), pp. 3257–60.

Daves, G. D., et al. "1,2–Additions to Heteroatom–Substituted Olefins by Organopalladium Reagents," *Chem. Rev.,* 1989, vol. 89, pp. 1433–1445.

Estel, L. et al. (Lab Chim. Org. Fine Heterocycl., INSA–IR-COF, Mont–Saint–Aignan, 76130, Fr.), "Synthesis of Ortho– Substituted Aminopyridines. Metalation of Pivaloylamino Derivatives." *J. Heterocycl. Chem.,* 1989, 26, pp. 105–112.

Kost, A. N., et al. "2–Methyl–5–ethynylpyridine," *Chemical Abstracts,* 1966, vol. 64, pp. 15830–15831.

Kost, A. N., et al. "Properties of the acetylene group bound to a pyridine ring," *Chemical Abstracts,* vol. 54, p. 11015.

March, *J. Advanced Org. Chem.,* 1985, 3rd Edition, pp. 461–462.

Murray, T. J., et al. *Tetrahedron,* 1995, 51 (2), pp. 635–648.

Nakane, M., et al. "Biosynthetic Studies of Secondary Plant Metabolites with $^{13}CO_2$–Nicotiana Alkaloids. 2. [1] New Synthesis of Nornicotine and Nicotine. Quantitative Carbon–13 NMR Spectroscopic Analysis of [2',3', N–$CH_3$–$^{13}C_3$]Nicotine[2]," *J. Org. Chem.,* 1978, vol. 43, No. 20, pp. 3922–3931.

Nakazato, et al. *Chemical Abstracts,* 1996, vol. 124: 317131a, No. 23.

Neef, H. et al. "Improved Synthesis of $N^1$–Pyridylthiamine Pyrophosphate, A Coenzymatically Active Analog of Thiamine Pyrophosphate." (Sekt. Biowiss Biotech., Univ. Halle–Wittenberg, Halle, DDR–4020, Ger. Dem. Rep.), *Liebigs Ann. Chem.* 1990, (9), pp. 913–916.

*Primary Examiner*—Jane Fan
*Attorney, Agent, or Firm*—Peter C. Richardson; Gregg C. Benxon; Jennifer A. Kispert

[57] ABSTRACT

The present invention relates to certain compounds of the formula (I),

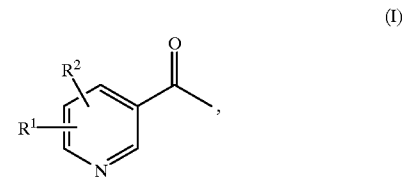

which are useful in the synthesis of certain β-adrenergic receptor agonists. The invention also relates to a process for synthesizing the compounds of formula (I) and to compounds of the formula (II),

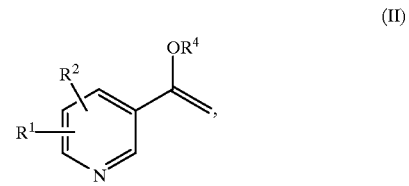

wherein $R^1$, $R^2$ and $R^4$ are defined herein, which are useful in the synthesis of the compounds of formula (I). The invention also relates to a process for synthesizing a compound of formula (II). The invention further relates to processes for synthesizing compounds of formula (Z*),

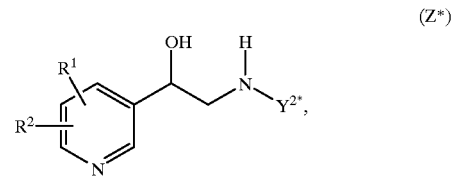

$R^1$, $R^2$ and $Y^{2*}$ are defined herein.

1 Claim, No Drawings

SUBSTITUTED PYRIDINES

CROSS REFERENCE TO RELATED APPLICATION

This is a division of commonly assigned U.S. patent application Ser. No. 08/968,129, filed on Nov. 12, 1997 now abandoned, which claims priority from U.S. patent application Ser. No. 60/030,802, filed on Nov. 14, 1996, now abandoned.

BACKGROUND OF THE INVENTION

The present invention relates to certain compounds of the formula (I) depicted below, which are useful in the synthesis of certain β-adrenergic receptor agonists having the general formula Z

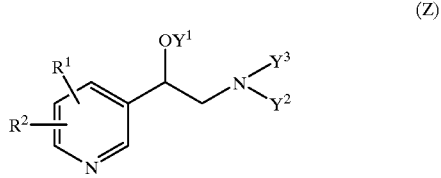

(Z)

where $R^1$ and $R^2$ are as defined herein for the compound of formula (I) and $Y^1$, $Y^2$ and $Y^3$ are any chemical substituents which can be attached to the atoms to which $Y^1$, $Y^2$ and $Y^3$ are attached and confer β-adrenergic receptor activity and as such have utility as hypoglycemic and antiobesity agents, $Y^1$ is preferably hydrogen. Examples of such substituents and the resultant β-adrenergic receptor agonists can be found in PCT Publication No. WO 94/29290 published Dec. 22, 1994. The invention also relates to a process for synthesizing the compounds of formula (I) and to compounds of the formula (II), defined hereinbelow, which are useful in the synthesis of the compounds of formula (I). The invention also relates to a process for synthesizing a compound of formula (II). The invention further relates to processes for synthesizing compounds of formula (Z*), defined hereinbelow. The β-adrenergic receptor agonists also possess utility for increasing lean meat deposition and/or improving the lean meat to fat ratio in edible animals.

The β-adrenergic receptor agonists further possess utility in the treatment of intestinal motility disorders, depression, prostate disease, dyslipidemia, and airway inflammatory disorders such as asthma and obstructive lung disease.

The disease diabetes mellitus is characterized by metabolic defects in production and/or utilization of carbohydrates which result in the failure to maintain appropriate blood sugar levels. The result of these defects is elevated blood glucose or hyperglycemia. Research in the treatment of diabetes has centered on attempts to normalize fasting and postprandial blood glucose levels. Current treatments include administration of exogenous insulin, oral administration of drugs and dietary therapies.

Two major forms of diabetes mellitus are recognized. Type I diabetes, or insulin-dependent diabetes, is the result of an absolute deficiency of insulin, the hormone which regulates carbohydrate utilization. Type II diabetes, or non-insulin dependent diabetes, often occurs with normal, or even elevated levels of insulin and appears to be the result of the inability of tissues to respond appropriately to insulin. Most of the Type II diabetics are also obese.

The β-adrenergic receptor agonists effectively lower blood glucose levels when administered orally to mammals with hyperglycemia or diabetes.

The β-adrenergic receptor agonists also reduce body weight or decrease weight gain when administered to mammals and poultry. The ability of β-adrenergic receptor agonists to affect weight gain is due to activation of β-adrenergic receptors which stimulate the metabolism of adipose tissue.

β-Adrenergic receptors have been categorized into $β_1$-, $β_2$- and $β_3$-subtypes. Agonists of β-receptors promote the activation of adenyl cyclase. Activation of $β_1$-receptors invokes increases in heart rate while activation of $β_2$-receptors induces relaxation of skeletal muscle tissue which produces a drop in blood pressure and the onset of smooth muscle tremors. Activation of $β_3$-receptors is known to stimulate lipolysis (the breakdown of adipose tissue triglycerides to glycerol and free fatty acids) and metabolic rate (energy expenditure), and thereby promote the loss of fat mass. Compounds that stimulate β-receptors are, therefore, useful as anti-obesity agents, and can also be used to increase the content of lean meat in edible animals. In addition, compounds which are $β_3$-receptor agonists have hypoglycemic or anti-diabetic activity, but the mechanism of this effect is unknown.

Until recently $β_3$-adrenergic receptors were thought to be found predominantly in adipose tissue. $β_3$-receptors are now known to be located in such diverse tissues as the intestine (J. Clin. Invest., 91, 344 (1993)) and the brain (Eur. J. Pharm., 219,193 (1992)). Stimulation of the $β_3$-receptor has been demonstrated to cause relaxation of smooth muscle in colon, trachea and bronchi. Life Sciences, 44(19), 1411 (1989); Br. J. Pharm., 112, 55 (1994); Br. J. Pharmacol., 110, 1311 (1993). For example, stimulation of $β_3$-receptors has been found to induce relaxation of histamine-contracted guinea pig ileum, J. Pharm. Exp. Ther., 260, 1, 192 (1992).

The $β_3$-receptor is also expressed in human prostate. Because stimulation of the $β_3$-receptor causes relaxation of smooth muscles that have been shown to express the $β_3$-receptor (e.g. intestine), one skilled in the art would predict relaxation of prostate smooth muscle. Therefore, $β_3$-agonists will be useful for the treatment or prevention of prostate disease.

Examples of β-adrenergic receptor agonists which can be synthesized using the compounds of formula (I) can be found in PCT Publication No. WO 94/29290 published Dec. 22, 1994, U.S. patent application Ser. No. 08/312,027 filed Sep. 26, 1994, PCT Application No. PCT/IB95/00344 filed May 10, 1995 and U.S. Provisional Application No. 60/015,216 filed Apr. 9, 1996, all of which are assigned to the assignee hereof.

With regard to the process for synthesizing a compound of formula (II), defined hereinbelow, of the present invention, the chemical literature teaches that the addition of aryl halides (for example, bromobenzene, PhBr) to a vinyl ether of formula (IV) (see below) (for example, n-butyl vinyl ether when $R_4$ is n-butyl) generally proceeds to afford a mixture of regioisomeric addition products resulting from addition of the aryl residue to either of the olefinic carbon atoms in the vinyl ether (Hallberg and Daves, Chemical Reviews, Vol. 89, 1989, page 1433). Thus, with bromobenzene and n-butyl vinyl ether, the addition products may be represented as PhCH=CHOBu and PhC(OBu)=CH$_2$. The product PhCH=CHOBu results from what is referred to as beta-arylation, in which the aryl group adds to the olefinic carbon atom distal to the oxygen atom of the vinyl ether. The product PhC(OBu)=CH$_2$ results from what is referred to as alpha-arylation, in which the aryl group adds to the olefinic carbon atom bonded to the oxygen atom of the vinyl ether. Furthermore, it has been well documented that when the aryl halide is substituted by electron withdrawing groups, such as the nitro group (for example, 4-bromo-1-nitrobenzene), the addition to the vinyl ether proceeds in such a way as to preferentially form the product of beta-arylation, $O_2NC_6H_4CH=CHOBu$, with the ratio of beta to alpha arylation generally exceeding 3 to 1 (Hallberg, Daves, and Andersson, *Journal of Organic Chemistry*, Vol. 52, 1987, 3529).

The chemistry of pyridines is frequently presented and thought of as being comparable to that of the corresponding nitrobenzenes, because of the significant electron deficiency of these ring systems, produced by the ring nitrogen atom in the case of pyridines and by the nitro substituent in the case of the nitrobenzenes (March, *Advanced Organic Chemistry*, 3rd Edition, 1985, page 461; Acheson, *The Chemistry of Heterocyclic Compounds*, 1960, page 167). Thus pyridines and the corresponding nitrobenzene analogs undergo many of the same reactions that are usual in benzene chemistry, such as nucleophilic aromatic substitution, and fail many of the same reactions that are common in benzene chemistry, such as electrophilic aromatic substitution.

It will be apparent to one of ordinary skill in the art that, for the purposes of the present invention, the product of alpha arylation, which is represented by formula II, is required in order to furnish the desired compounds of formula (I) upon hydrolysis of the vinyl ether. Thus, one skilled in the art would not anticipate that pyridyl halides, such as those of formula (III), would afford synthetically useful quantities of the alpha-arylation products of formula (II).

SUMMARY OF THE INVENTION

This invention relates to compounds having the formula (I),

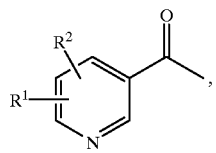

(I)

and the racemic-enantiomeric mixtures and optical isomers of said compounds, wherein $R^1$ is selected from the group consisting of —$NR^3$—CO—($C_1$–$C_{10}$)alkyl, —$NR^3$—$CO_2$—($C_1$–$C_{10}$)alkyl, —$NR^3$—$CO_2$—$(CH_2)_a$-(optionally substituted phenyl), —$NR^3$—CO—$(CH_2)_a$-(optionally substituted phenyl), —$NR^3$—$SO_2$—($C_1$–$C_{10}$)alkyl, —$NR^3$—$SO_2$—$(CH_2)_a$-(optionally substituted phenyl) and —$NR^3$—CO—($C_1$–$C_4$)perfluoroalkyl;

$R^2$ is selected from the group consisting of hydrogen, amino, nitro, ($C_1$–$C_8$)alkylamino, fluoro, $CF_3$, ($C_1$–$C_4$)alkyl, ($C_1$–$C_4$)alkoxy, —$NR^3$—CO—($C_1$–$C_{10}$)alkyl, —$NR^3$—$CO_2$—($C_1$–$C_{10}$)alkyl, —$NR^3$—$CO_2$—$(CH_2)_a$-(optionally substituted phenyl), —$NR^3$—CO—$(CH_2)_a$-(optionally substituted phenyl), —$NR^3$—$SO_2$—($C_1$–$C_{10}$)alkyl, —$NR^3$—$SO_2$—$(CH_2)_a$-(optionally substituted phenyl) and —$NR^3$—CO—($C_1$–$C_4$)perfluoroalkyl;

where a for each occurrence is independently 0, 1, 2, 3 or 4;

$R^3$ for each occurrence is independently selected from the group consisting of hydrogen and ($C_1$–$C_6$) alkyl; and the optionally substituted phenyl group is optionally substituted with one, two or three substituents, each substituent is independently selected from the group consisting of hydroxy, fluoro, chloro, iodo, bromo, $CF_3$, sulfonamide, ($C_1$–$C_4$)alkyl, ($C_1$–$C_4$)alkoxy, carboxy, hydroxyalkyl, ($C_1$–$C_4$)alkoxycarbonyl, ($C_1$–$C_4$) thioalkyl, sulfonyl, sulfinyl and amino;

provided that a compound of formula (I) is not N-(5-acetyl-2-methyl-4-pyridinyl)acetamide, 3-acetyl-4-(pivaloylamino)pyridine or 3-acetyl-2-(pivaloylamino) pyridine.

A preferred group of compounds of formula (I), designated "Group A", are those compounds of formula (I) wherein $R^1$ is selected from the group consisting of —$NR^3$—$CO_2$—$(CH_2)_a$-(optionally substituted phenyl), —$NR^3$—CO—$(CH_2)_a$-(optionally substituted phenyl), —$NR^3$—$SO_2$—($C_1$–$C_{10}$)alkyl, —$NR^3$—$SO_2$—$(CH_2)_a$-(optionally substituted phenyl) and —$NR^3$—CO—($C_1$–$C_4$)perfluoroalkyl; and $R^2$ is selected from the group consisting of hydrogen, ($C_1$–$C_4$)alkyl and ($C_1$–$C_4$)alkoxy.

A preferred group of compounds of Group A, designated "Group B", are those compounds of group A wherein $R^1$ is selected from the croup consisting of —$NR^3$—$CO_2$—$(CH_2)_a$-(optionally substituted phenyl) and —$NR^3$—CO—($C_1$–$C_4$)perfluoroalkyl.

A preferred group of compounds of Group B, designated "Group C", are those compounds of Group B wherein $R^2$ is selected from the group consisting of hydrogen, methyl and methoxy.

A preferred group of compounds of Group C, designated "Group D", are those compounds of Group C wherein $R^1$ isselected from the group consisting of —NH—$CO_2$—$CH_2$—(phenyl) and —NH—CO—$CF_3$.

A preferred group of compounds of Group D, designated "Group E", are those compounds of Group D wherein $R^2$ is hydrogen.

Of the Group E compounds, (5-acetyl-pyridin-2-yl)-carbamic acid benzyl ester and N-(5-acetyl-pyridin-2-yl)-2, 2,2-trifluoro-acetamide are especially preferred.

Another preferred group of compounds of formula (I), designated "Group F", are those compounds of formula (I) wherein $R^1$ is —$NR^3$—CO—($C_1$–$C_4$)alkyl and $R^2$ is ($C_1$–$C_4$)alkyl.

A preferred group of compounds of Group F, designated "Group G", are those compounds of Group F wherein $R^1$ is —NH—CO—$CH_3$ and $R^2$ is methyl.

Of the Group G compounds, N-(5-acetyl-6-methyl-pyridin-2-yl)-acetamide, N-(3-acetyl-5-methyl-pyridin-2-yl)-acetamide and N-(5-acetyl-3-methyl-pyridin-2-yl)-acetamide are especially preferred.

Yet another preferred group of compounds of formula (I), designated "Group H", are those compounds of formula (I) wherein $R^1$ is —NH—CO—($C_1$–$C_4$)alkyl and $R^2$ is hydrogen.

Of the Group H compounds, N-(5-acetyl-pyridin-2-yl)-, acetamide and N-(5-acetyl-pyridin-2-yl)-2,2-dimethyl-propionamide are especially preferred.

This invention also relates to intermediate compounds of formula (II),

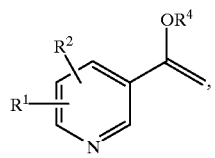

(II)

which are useful in the synthesis of the compounds of formula (I), as defined herein, wherein $R^1$ is selected from the group consisting of —NR$^3$—CO—(C$_1$–C$_{10}$)alkyl, —NR$^3$—CO$_2$—(C$_1$–C$_{10}$)alkyl, —NR$^3$—CO$_2$—(CH$_2$)$_a$-(optionally substituted phenyl), —NR$^3$—CO—(CH$_2$)$_a$-(optionally substituted phenyl), —NR$^3$—SO$_2$—(C$_1$–C$_{10}$)alkyl, —NR$^3$—SO$_2$—(CH$_2$)$_a$-(optionally substituted phenyl) and —NR$^3$—CO—(C$_1$–C$_4$)perfluoroalkyl;

$R^2$ is selected from the group consisting of hydrogen, amino, nitro, (C$_1$–C$_8$)alkylamino, fluoro, CF$_3$, (C$_1$–C$_4$)alkyl, (C$_1$–C$_4$)alkoxy, —NR$^3$—CO—(C$_1$–C$_{10}$)alkyl, —NR$^3$—CO$_2$—(C$_1$–C$_{10}$)alkyl, —NR$^3$—CO$_2$—(CH$_2$)$_a$-(optionally substituted phenyl), —NR$^3$—CO—(CH$_2$)$_a$-(optionally substituted phenyl), —NR$^3$—SO$_2$—(C$_1$–C$_{10}$)alkyl, —NR$^3$—SO$_2$—(CH$_2$)$_a$-(optionally substituted phenyl) and —NR$^3$—CO—(C$_1$–C$_4$)perfluoroalkyl;

where a for each occurrence is independently 0, 1, 2, 3 or 4;

$R^3$ for each occurrence is independently selected from the group consisting of hydrogen and (C$_1$–C$_6$)alkyl; and the optionally substituted phenyl group is optionally substituted with one, two or three substituents, each substituent is independently selected from the group consisting of hydroxy, fluoro, chloro, iodo, bromo, CF$_3$, sulfonamide, (C$_1$–C$_4$)alkyl, (C$_1$–C$_4$)alkoxy, carboxy, hydroxyalkyl, (C$_1$–C$_4$)alkoxycarbonyl, (C$_1$–C$_4$)thioalkyl, sulfonyl, sulfinyl and amino; and $R^4$ is (C$_1$–C$_6$)alkyl.

The present invention also relates to a process for the preparation of a compound of formula (II),

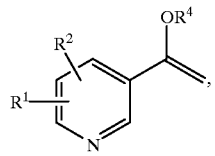

(II)

comprising, reacting a compound of formula (III),

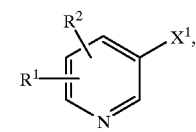

(III)

with a vinyl ether of formula (IV), CH$_2$=CHOR$^4$, in the presence of a palladium compound or a palladium metal catalyst and a base;

wherein $X^1$ is bromo, iodo, methanesulfonyloxy, or trifluoromethanesulfonyloxy;

$R^1$ is selected from the group consisting of —NR$^3$—CO—(C$_1$–C$_{10}$)alkyl, —NR$^3$—CO$_2$—(C$_1$–C$_{10}$)alkyl, —NR$^3$—CO$_2$—(CH$_2$)$_a$-(optionally substituted phenyl), —NR$^3$—CO—(CH$_2$)$_a$-(optionally substituted phenyl), —NR$^3$—SO$_2$—(C$_1$–C$_{10}$)alkyl, —NR$^3$—SO$_2$—(CH$_2$)$_a$-(optionally substituted phenyl) and —NR$^3$—CO—(C$_1$–C$_4$)perfluoroalkyl;

$R^2$ is selected from the group consisting of hydrogen, amino, nitro, (C$_1$–C$_8$)alkylamino, fluoro, CF$_3$, (C$_1$–C$_4$)alkyl, (C$_1$–C$_4$)alkoxy, —NR$^3$—CO—(C$_1$–C$_{10}$)alkyl, —NR$^3$—CO$_2$—(C$_1$–C$_{10}$)alkyl, —NR$^3$—CO$_2$—(CH$_2$)$_a$-(optionally substituted phenyl), —NR$^3$—CO—(CH$_2$)$_a$-(optionally substituted phenyl), —NR$^3$—SO$_2$—(C$_1$–C$_{10}$)alkyl, —NR$^3$—SO$_2$—(CH$_2$)$_a$-(optionally substituted phenyl) and —NR$^3$—CO—(C$_1$–C$_4$)perfluoroalkyl;

where a for each occurrence is independently 0, 1, 2, 3 or 4;

$R^3$ for each occurrence is independently selected from the group consisting of hydrogen and (C$_1$–C$_6$)alkyl;

the optionally substituted phenyl group is optionally substituted with one, two or three substituents, each substituent is independently selected from the group consisting of hydroxy, fluoro, chloro, iodo, bromo, CF$_3$, sulfonamide, (C$_1$–C$_4$)alkyl, (C$_1$–C$_4$)alkoxy, carboxy, hydroxyalkyl, (C$_1$–C$_4$)alkoxycarbonyl, (C$_1$–C$_4$)thioalkyl, sulfonyl, sulfinyl and amino; and $R^4$ is (C$_1$–C$_6$)alkyl; provided that when $X^1$ is Br, the reaction is conducted in the presence of a phosphine.

A preferred process of the immediately foregoing process is a process wherein $R^1$ is —NHCOCH$_3$, —NHCO-t-Bu, —NHCOCF$_3$ or —NHCOO—CH$_2$-phenyl; and $R^2$ is hydrogen or methyl.

A preferred process of the immediately foregoing process is a process wherein $X^1$ is Br and the reaction is conducted also in the presence of a phosphine compound.

A preferred process of the immediately foregoing process is a process wherein the reaction is conducted also in the presence of a polar aprotic solvent.

A preferred process of the immediately foregoing process is a process wherein the reaction of the compound of formula (III) with the vinyl ether of formula (IV), CH$_2$=CHOR$^4$, is conducted at about 20° to about 130° C., the palladium catalyst is a palladium (II) compound, and the phosphine is a triarylphosphine.

A preferred process of the immediately foregoing process is a process wherein the reaction is conducted at about 60° C. to about 100° C., the phosphine is tri-o-tolylphosphine, and the solvent is acetonitrile.

The present invention also relates to a process for the preparation of a compound of formula (I),

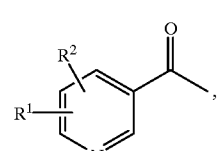

(I)

comprising, reacting a compound of formula (II),

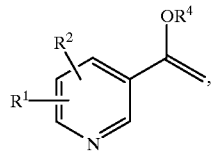
(II)

with an acid in the presence of water;
wherein
$R^1$ is selected from the group consisting of —$NR^3$—CO—($C_1$–$C_{10}$)alkyl, —$NR^3$—$CO_2$—($C_1$–$C_{10}$)alkyl, —$NR^3$—$CO_2$—$(CH_2)_a$-(optionally substituted phenyl), —$NR^3$—CO—$(CH_2)_a$-(optionally substituted phenyl), —N$R^3$—$SO_2$—($C_1$–$C_{10}$)alkyl, —$NR^3$—$SO_2$—$(CH_2)_a$-(optionally substituted phenyl) and —$NR^3$—CO—($C_1$–$C_4$)perfluoroalkyl;

$R^2$ is selected from the group consisting of hydrogen, amino, nitro, ($C_1$–$C_8$)alkylamino, fluoro, $CF_3$, ($C_1$–$C_4$)alkyl, ($C_1$–$C_4$)alkoxy, —$NR^3$—CO—($C_1$–$C_{10}$)alkyl, —$NR^3$—$CO_2$—($C_1$–$C_{10}$)alkyl, —$NR^3$—$CO_2$—$(CH_2)_a$-(optionally substituted phenyl), —$NR^3$—CO—$(CH_2)_a$-(optionally substituted phenyl), —$NR^3$—$SO_2$—($C_1$–$C_{10}$)alkyl, —$NR^3$—$SO_2$—$(CH_2)_a$-(optionally substituted phenyl) and —$NR^3$—CO—($C_1$–$C_4$)perfluoroalkyl;

where a for each occurrence is independently 0, 1, 2, 3 or 4;

$R^3$ for each occurrence is independently selected from the group consisting of hydrogen and ($C_1$–$C_6$)alkyl;

optionally substituted phenyl group is optionally substituted with one, two or three substituents, each substituent is independently selected from the group consisting of hydroxy, fluoro, chloro, iodo, bromo, $CF_3$, sulfonamide, ($C_1$–$C_4$)alkyl, ($C_1$–$C_4$)alkoxy, carboxy, hydroxyalkyl, ($C_1$–$C_4$)alkoxycarbonyl, ($C_1$–$C_4$) thioalkyl, sulfonyl, sulfinyl and amino; and $R^4$ is ($C_1$–$C_6$)alkyl.

A preferred process of the immediately foregoing process is where the compound of formula (I) is (5-acetyl-pyridin-2-yl)-carbamic acid benzyl ester, N-(5-acetyl-pyridin-2-yl)-2,2,2-trifluoro-acetamide, N-(5-acetyl-6-methyl-pyridin-2-yl)-acetamide, N-(3-acetyl-5-methyl-pyridin-2-yl)-acetamide, N-(5-acetyl-3-methyl-pyridin-2-yl)-acetamide, N-(5-acetyl-pyridin-2-yl)-acetamide or N-5-acetyl-pyridin-2-yl)-2,2-dimethylpropionamide.

This invention also provides a process for the preparation of a compound of the formula (Z*),

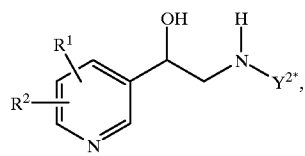
(Z*)

and the racemic-enantiomeric mixtures and optical isomers of said compounds comprising, (1) reacting a compound of formula (I),

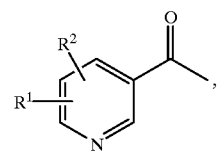
(I)

with a bromine, chlorine or iodine source to form a compound of formula (a),

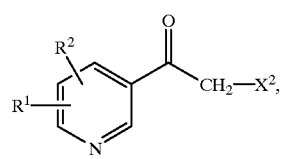
(a)

(2) reacting a compound of formula (a) with a compound of formula $H_2N$—$Y^{2*}$ to form a compound of formula ($Z^1$),

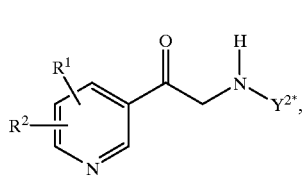
($Z^1$)

and (3) reacting a compound of formula ($Z^1$) with a reducing agent to form a compound of formula (Z*) and the racemic-enantiomeric mixtures and optical isomers of said compound of formula (Z*), wherein
$X^2$ is Cl, Br or I;
$R^1$ is selected from the group consisting of —$NR^3$—CO—($C_1$–$C_{10}$)alkyl, —$NR^3$—$CO_2$—($C_1$–$C_{10}$)alkyl, —$NR^3$—$CO_2$—$(CH_2)_a$-(optionally substituted phenyl), —$NR^3$—CO—$(CH_2)_a$-(optionally substituted phenyl), —N$R^3$—$SO_2$—($C_1$–$C_{10}$)alkyl, —$NR^3SO_2$—$(CH_2)_a$-(optionally substituted phenyl) and —$NR^3$—CO—($C_1$–$C_4$)perfluoroalkyl;

$R^2$ is selected from the group consisting of hydrogen, amino, nitro, ($C_1$–$C_8$)alkylamino, fluoro, $CF_3$, ($C_1$–$C_4$)alkyl, ($C_1$–$C_4$)alkoxy, —$NR^3$—CO—($C_1$–$C_{10}$)alkyl, —$NR^3$—$CO_2$—($C_1$–$C_{10}$)alkyl, —$NR^3$—$CO_2$—$(CH_2)_a$-(optionally substituted phenyl), —$NR^3$—CO—$(CH_2)_a$-(optionally substituted phenyl), —$NR^3$—$SO_2$—($C_1$–$C_{10}$)alkyl, —$NR^3$—$SO_2$—$(CH_2)_a$- (optionally substituted phenyl) and —$NR^3$—CO—($C_1$–$C_4$)perfluoroalkyl;

where a for each occurrence is independently 0, 1, 2, 3 or 4;

$R^3$ for each occurrence is independently selected from the group consisting of hydrogen and ($C_1$–$C_6$)alkyl; and the optionally substituted phenyl group is optionally substituted with one, two or three substituents, each substituent is independently selected from the group consisting of hydroxy, fluoro chloro, iodo, bromo, $CF_3$, sulfonamide, ($C_1$–$C_4$)alkyl, ($C_1$–$C_4$)alkoxy, carboxy, hydroxyalkyl, ($C_1$–$C_4$)alkoxycarbonyl, ($C_1$–$C_4$) thioalkyl, sulfonyl, sulfinyl and amino;

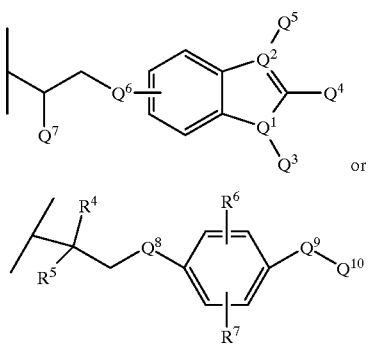

$Y^{2*}$ is wherein $Q^1$ is oxygen, nitrogen or sulfur;

$Q^2$ is carbon or nitrogen;

$Q^3$ is hydrogen, —$(CH_2)_n$-phenyl, —$(C_1-C_{10})$alkyl, —$(CH_2)_n$—$NG^1G^2$, —$(CH_2)_n$—$CO_2G^3$, —$(CH_2)_n$—CO—$NG^1G^2$, —$(CH_2)_n$—$OG^3$, —$(CH_2)_nSO_3G^3$, —$(CH_2)_n$—$SO_2$—$(C_1-C_6)$alkyl, —$(CH_2)_n$—$SO_2NG^1G^2$, or a heterocycle selected from the group consisting of —$(CH_2)_n$-pyridyl, —$(CH_2)_n$-pyrimidyl, —$(CH_2)_n$-pyrazinyl, —$(CH_2)_n$-isxazolyl, —$(CH_2)_n$-oxazolyl, —$(CH_2)_n$-thiazolyl, —$(CH_2)_n$-(1,2,4-oxadiazolyl), —$(CH_2)_n$-imidazolyl, —$(CH_2)_n$-triazolyl and —$(CH_2)_n$-tetrazolyl;

wherein one of the ring nitrogen atoms of said —$(CH_2)_n$-imidazolyl, —$(CH_2)_n$-triazolyl and —$(CH_2)_n$-tetrazolyl may optionally be substituted by $(C_1-C_8)$alkyl optionally independently substituted with one or more halo atoms;

wherein each of said heterocycles may optionally be substituted on one or more of the ring carbon atoms by one or more substituents independently selected from the group consisting of $(C_1-C_8)$alkyl optionally independently substituted with one or more halo atoms, halo, nitro, cyano, —$(CH_2)_n$—$NG^1G^2$, —$(CH_2)_n$—$CO_2G^3$, —$(CH_2)_n$—CO—$NG^1G^2$, —$(CH_2)_n$—$OG^3$, —$(CH_2)_n$—$SO_2G^3$, —$(CH_2)_n$—$SO_2$—$(C_1-C_6)$alkyl and —$(CH_2)_n$—$SO_2NG^1G^2$;

wherein the phenyl moiety of said —$(CH_2)_n$-phenyl may optionally be substituted with one or more substituents independently selected from the group consisting of $(C_1-C_6)$alkyl optionally independently substituted with one or more halo atoms, hydroxy, $(C_1-C_6)$alkoxy optionally independently substituted with one or more halo atoms, $(C_1-C_6)$alkylthio, fluoro, chloro, bromo, iodo, cyano, nitro, —$(CH_2)_n$—$NG^1G^2$, —$(CH_2)_n$—$CO_2G^3$, —$(CH_2)_n$—CO—$NG^1G^2$, —$(CH_2)_n$—$OG^3$, —$(CH_2)_n$—$SO_3G^3$, —$(CH_2)_n$—$SO_2$—$(C_1-C_6)$alkyl, —$(CH_2)_n$——$SO_2NG^1G^2$; —$(CH_2)_n$—$NG^3SO_2G^3$ and —$(CH_2)_n$—$NG^3$—$SO_2$—$NG^1G^2$;

$Q^4$ is —$(CH_2)_n$—CN, —$(CH_2)_nCO_2G^3$, —$(CH_2)_n$—$SO_3G^3$, —$(CH_2)_n$—$SO_2$—$(C_1-C_6)$alkyl, —$(CH_2)_n$—$SO_2NG^1G^2$, —$(CH_2)_nCH_2OH$, —$(CH_2)_n$—CHO, —$(CH_2)_n$—CO—$G^3$, —$(CH_2)_n$—$CONG^1G^2$, or a heterocycle selected from —$(CH_2)_n$-thiazolyl, —$(CH_2)_n$-oxazolyl, —$(CH_2)_n$-imidazolyl, —$(CH_2)_n$-triazolyl, —$(CH_2)_n$-1,2,4-oxadiazolyl, —$(CH_2)_n$-isoxazolyl, —$(CH_2)_n$-tetrazolyl and —$(CH_2)_n$-pyrazolyl;

wherein one of the ring nitrogen atoms of said —$(CH_2)_n$-imidazolyl, —$(CH_2)_n$-triazolyl and —$(CH_2)_n$-tetrazolyl may optionally be substituted by $(C_1-C_6)$alkyl optionally independently substituted with one or more halo atoms;

wherein each of said heterocycles may optionally be substituted on one or more of the ring carbon atoms by one or more substituents independently selected from the group consisting of hydrogen, $(C_1-C_6)$alkyl optionally independently substituted with one or more halo atoms, —$(CH_2)_n$—CO—$NG^1G^2$, —$(CH_2)_n$—$CO_2G^3$, halo, nitro, cyano, —$(CH_2)_n$—CO—$NG^1G^2$, —$(CH_2)_n$—$OG^3$, —$(CH_2)_nSO_3G^3$, —$(CH_2)_nSO_2$—$(C_1-C_6)$alkyl, or —$(CH_2)_n$—$SO_2NG^1G^2$;

$Q^5$ is hydrogen or $(C_1-C_6)$alkyl optionally independently substituted with one or more halo atoms;

$Q^6$ is a covalent bond, oxygen or sulfur;

$Q^7$ is hydrogen or $(C_1-C_6)$alkyl optionally independently substituted with one or more halo atoms;

$Q^8$ and $Q^9$ are independently a covalent bond, oxygen, sulfur, NH or —N—$(C_1-C_6)$alkyl;

$Q^{10}$ is —$(CH_2)_mOR^9$, —$(CH_2)_nCO_2H$, —$(CH_2)_nCOR^{11}$, —$(CH_2)_nSO_2NR^9R^{10}$, —$(CH_2)_n$—$NR^9SO_2R^8$, —$(CH_2)_nP(O)(OR^4)(OR^5)$, —$(CH_2)_n$—O—$(CH_2)_mCO_2H$, —$(CH_2)_n$—O—$(CH_2)_mCOR^{11}$, —$(CH_2)_n$—O—$(CH_2)_mP(O)(OR^4)(OR^5)$, —$(CH_2)_n$—O—$(CH_2)_mSO_2NR^9R^{10}$, or —$(CH_2)_n$—O—$(CH_2)_m$—$NR^9SO_2R^8$;

$R^4$ and $R^5$ are each independently hydrogen or $(C_1-C_6)$alkyl; and $R^6$ and $R^7$ are each independently hydrogen, halo, $(C_1-C_6)$alkyl, nitro, cyano, trifluoromethyl, $SO_2R^8$, $SO_2NR^9R^{10}$, $NR^9R^{10}$, $COR^{11}$, $CO_2R^9$, $(C_1-C_6)$alkoxy, $NR^9SO_2R^8$, $NR^9COR^{11}$, $NR^9COR^9$ or $OR^9$;

where $G^1$ and $G^2$ for each occurrence are each independently hydrogen, $(C_1-C_6)$alkyl optionally independently substituted with one or more halo, $(C_1-C_8)$alkoxy$(C_1-C_6)$alkyl or $(C_3-C_8)$cycloalkyl, or $G^1$ and $G^2$ together with the nitrogen to which they are attached form a saturated heterocyclic ring having from 3 to 7 carbon atoms wherein one of said carbon atoms may optionally be replaced by oxygen, nitrogen or sulfur;

$G^3$ for each occurrence is independently hydrogen or $(C_1-C_6)$alkyl;

$R^8$ for each occurrence is independently $(C_1-C_6)$alkyl or $(C_1-C_6)$alkoxy$(C_1-C_6)$alkyl;

$R^9$ and $R^{10}$ for each occurrence are independently hydrogen, $(C_1-C_6)$alkyl, $(C_3-C_8)$cycloalkyl, or $(C_1-C_6)$alkoxy$(C_1-C_6)$alkyl;

$R^{11}$ for each occurrence is independently hydrogen, $(C_1-C_6)$alkyl, $NR^9R^{10}$, $(C_3-C_8)$cycloalkyl, or $(C_1-C_6)$alkoxy$(C_1-C_6)$alkyl wherein $R^9$ and $R^{10}$ are as defined above;

m for each occurrence is independently an integer of 1 to 6; and n for each occurrence is independently 0 or an integer of 1 to 6;

with the provisos that:

(1) when $Q^9$ is O or S then n is not 0;

(2) when $Q^1$ is oxygen or sulfur then $Q^3$ is absent; and (3) when $Q^2$ is nitrogen then $Q^5$ is absent.

A preferred process of the immediately foregoing process is where $R^1$ is —$NHCOCH_3$, —NHCO-t-Bu, —$NHCOCF_3$ or —NHCOO—$CH_2$-phenyl; and $R^2$ is hydrogen or methyl.

This invention also provides another process for the preparation of a compound of the formula (Z*),

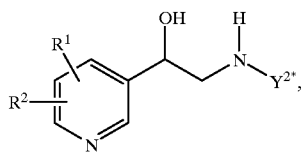

and the racemic-enantiomeric mixtures and optical isomers of said compounds comprising, (1) reacting a compound of formula (I),

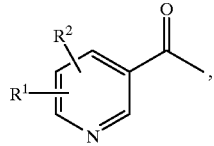

with a bromine, chlorine or iodine source to form a compound of formula (a),

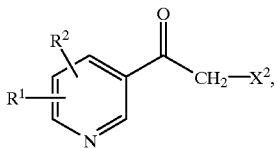

(2) reacting a compound of formula (a) with a mild reducing agent to form a compound of formula (c),

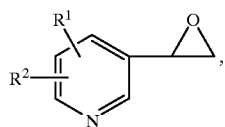

and (3) reacting a compound of formula (c) with a base and $H_2N-Y^{2*}$ to form a compound of formula ($Z^*$), wherein $X^2$ is Cl, Br or I;

$R^1$ is selected from the group consisting of —$NR^3$—CO—($C_1$–$C_{10}$)alkyl, —$NR^3$—$CO_2$—($C_1$–$C_{10}$)alkyl, —$NR^3$—$CO_2$—($CH_2$)$_a$-(optionally substituted phenyl), —$NR^3$—CO—($CH_2$)$_a$-(optionally substituted phenyl), —$NR^3$—$SO_2$—($C_1$–$C_{10}$)alkyl, —$NR^3$—$SO_2$—($CH_2$)$_a$-(optionally substituted phenyl) and —$NR^3$—CO—($C_1$–$C_4$) perfluoroalkyl;

$R^2$ is selected from the group consisting of hydrogen, amino, nitro, ($C_1$–$C_8$)alkylamino, fluoro, $CF_3$, ($C_1$–$C_4$)alkyl, ($C_1$–$C_4$)alkoxy, —$NR^3$—CO—($C_1$–$C_{10}$)alkyl, —$NR^3$—$CO_2$—($C_1$–$C_{10}$)alkyl, —$NR^3$—$CO_2$—($CH_2$)$_a$-(optionally substituted phenyl), —$NR^3$—CO—($CH_2$)$_a$-(optionally substituted phenyl), —$NR^3$—$SO_2$—($C_1$–$C_{10}$) alkyl, —$NR^3$—$SO_2$—($CH_2$)$_a$-(optionally substituted phenyl) and —$NR^3$—CO—($C_1$–$C_4$)perfluoroalkyl;

where a for each occurrence is independently 0, 1, 2, 3 or 4;

$R^3$ for each occurrence is independently selected from the group consisting of hydrogen and ($C_1$–$C_6$)alkyl; and the optionally substituted phenyl group is optionally substituted with one, two or three substituents, each substituent is independently selected from the group consisting of hydroxy, fluoro, chloro, iodo, bromo, $CF_3$, sulfonamide, ($C_1$–$C_4$)alkyl, ($C_1$–$C_4$)alkoxy, carboxy, hydroxyalkyl, ($C_1$–$C_4$)alkoxycarbonyl, ($C_1$–$C_4$) thioalkyl sulfonyl, sulfinyl and amino;

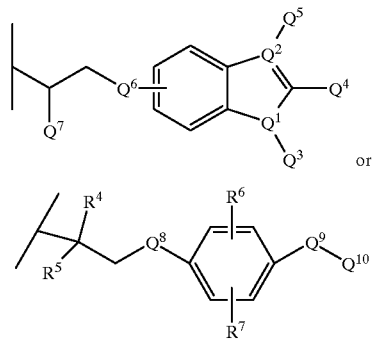

$Y^{2*}$ is or
wherein
$Q^1$ is oxygen, nitrogen or sulfur;
$Q^2$ is carbon or nitrogen;
$Q^3$ is hydrogen, —($CH_2$)$_n$-phenyl, —($C_1$–$C_{10}$)alkyl, —($CH_2$)$_n$—$NG^1G^2$, —($CH_2$)$_n$—$CO_2G^3$, —($CH_2$)$_n$—CO—$NG^1G^2$, —($CH_2$)$_n$—$OG^3$, —($CH_2$)$_n$—$SO_3G^3$, —($CH_2$)$_n$—$SO_2$—($C_1$–$C_6$)alkyl, —($CH_2$)$_n$—$SO_2NG^1G^2$, or a heterocycle selected from the group consisting of —($CH_2$)$_n$-pyridyl, —($CH_2$)$_n$-pyrimidyl, —($CH_2$)$_n$-pyrazinyl, —($CH_2$)$_n$-isoxazolyl, —($CH_2$)$_n$-oxazolyl, —($CH_2$)$_n$-thiazolyl, —($CH_2$)$_n$-(1,2,4-oxadiazolyl), —($CH_2$)$_n$-imidazolyl, —($CH_2$)$_n$-triazolyl and —($CH_2$)$_n$-tetrazolyl;

wherein one of the ring nitrogen atoms of said —($CH_2$)$_n$-imidazolyl, —($CH_2$)$_n$-triazolyl and —($CH_2$)$_n$-tetrazolyl may optionally be substituted by ($C_1$–$C_8$) alkyl optionally independently substituted with one or more halo atoms;

wherein each of said heterocycles may optionally be substituted on one or more of the ring carbon atoms by one or more substituents independently selected from the group consisting of ($C_1$–$C_8$)alkyl optionally independently substituted with one or more halo atoms, halo, nitro, cyano, —($CH_2$)$_n$—$NG^1G^2$, —($CH_2$)$_n$—$CO_2G^3$, —($CH_2$)$_n$—CO—$NG^1G^2$, —($CH_2$)$_n$—$OG^3$, —($CH_2$)$_n$—$SO_2G^3$, —($CH_2$)$_n$—$SO_2$—($C_1$–$C_6$)alkyl and —($CH_2$)$_n$—$SO_2NG^1G^2$;

wherein the phenyl moiety of said —($CH_2$)$_n$-phenyl may optionally be substituted with one or more substituents independently selected from the group consisting of ($C_1$–$C_6$)alkyl optionally independently substituted with one or more halo atoms, hydroxy, ($C_1$–$C_6$)alkoxy optionally independently substituted with one or more halo atoms, ($C_1$–$C_6$)alkylthio, fluoro, chloro, bromo, iodo, cyano, nitro, —($CH_2$)$_n$—$NG^1G^2$, —($CH_2$)$_n$—$CO_2G^3$, —($CH_2$)$_n$—CO—$NG^1G^2$, —($CH_2$)$_n$—$OG^3$, —($CH_2$)$_n$—$SO_3G^3$, —($CH_2$)$_n$—$SO_2$—($C_1$–$C_6$)alkyl, —($CH_2$)$_n$—$SO_2NG^1G^2$; —($CH_2$)$_n$—$NG^3$—$SO_2$—$G^3$ and —($CH_2$)$_n$—$NG^3$—$SO_2$—$NG^1G^2$;

$Q^4$ is —($CH_2$)$_n$—CN, —($CH_2$)$_n$$CO_2G^3$, —($CH_2$)$_n$—$SO_3G^3$, —($CH_2$)$_n$—$SO_2$—($C_1$–$C_6$)alkyl, —($CH_2$)$_n$—$SO_2NG^1G^2$, —($CH_2$)$_n$$CH_2$OH, —($CH_2$)$_n$—CHO, —($CH_2$)$_n$—CO—$G^3$, —($CH_2$)$_n$-CONG$^1G^2$, or a heterocycle selected from —($CH_2$)$_n$-thiazolyl, —($CH_2$)$_n$-oxazolyl, —($CH_2$)$_n$-imidazolyl, —$(CH_2)_n$-triazolyl, —$(CH_2)_n$-1,2,4-oxadiazolyl, —$(CH_2)_n$-isoxazolyl, —$(CH_2)_n$-tetrazolyl and —$(CH_2)_n$-pyrazolyl;
wherein one of the ring nitrogen atoms of said —$(CH_2)_n$-imidazolyl, —$(CH_2)_n$-triazolyl and —$(CH_2)_n$-tetrazolyl may optionally be substituted by $(C_1-C_6)$ alkyl optionally independently substituted with one or more halo atoms;

wherein each of said heterocycles may optionally be substituted on one or more of the ring carbon atoms by one or more substituents independently selected from the group consisting of hydrogen, $(C_1-C_6)$alkyl optionally independently substituted with one or more halo atoms, —$(CH_2)_n$—CO—$NG^1G^2$, —$(CH_2)_n$—$CO_2G^3$, halo, nitro, cyano, —$(CH_2)_n$—CO—$NG^1G^2$, —$(CH_2)_n$—$OG^3$, —$(CH_2)_n$—$SO_3G^3$, —$(CH_2)_n$—$SO_2$—$(C_1-C_6)$alkyl, or —$(CH_2)_n$—$SO_2NG^1G^2$;

$Q^5$ is hydrogen or $(C_1-C_6)$alkyl optionally independently substituted with one or more halo atoms;

$Q^6$ is a covalent bond, oxygen or sulfur;

$Q^7$ is hydrogen or $(C_1-C_6)$alkyl optionally independently substituted with one or more halo atoms;

$Q^8$ and $Q^9$ are independently a covalent bond, oxygen, sulfur, NH or N—$(C_1-C_6)$alkyl;

$Q^{10}$ is —$(CH_2)_mOR^9$, —$(CH_2)_nCO_2H$, —$(CH_2)_nCOR^{11}$, —$(CH_2)_nSO_2NR^9R^{10}$, —$(CH_2)_n$—$NR^9SO_2R^8$, —$(CH_2)_nP(O)(OR^4)(OR^5)$, —$(CH_2)_n$—O—$(CH_2)_mCO_2H$, —$(CH_2)_n$—O—$(CH_2)_mCOR^{11}$, —$(CH_2)_n$—O—$(CH_2)_mP(O)(OR^4)(OR^5)$, —$(CH_2)_n$—O—$(CH_2)_mSO_2NR^9R^{10}$, or —$(CH_2)_n$—O—$(CH_2)_m$—$NR^9SO_2R^8$;

$R^4$ and $R^5$ are each independently hydrogen or $(C_1-C_6)$ alkyl; and $R^6$ and $R^7$ are each independently hydrogen, halo, $(C_1-C_6)$ alkyl, nitro, cyano, trifluoromethyl, $SO_2R^8$, $SO_2NR^9R^{10}$, $NR^9R^{10}$, $COR^{11}$, $CO_2R^9$, $(C_1-C_6)$alkoxy, $NR^9SO_2R^8$, $NR^9COR^{11}$, $NR^9CO_2R^9$ or $OR^9$;

where $G^1$ and $G^2$ for each occurrence are each independently hydrogen, $(C_1-C_6)$alkyl optionally independently substituted with one or more halo, $(C_1-C_8)$alkoxy$(C_1-C_6)$alkyl or $(C_3-C_8)$cycloalkyl, or $G^1$ and $G^2$ together with the nitrogen to which they are attached form a saturated heterocyclic ring having from 3 to 7 carbon atoms wherein one of said carbon atoms may optionally be replaced by oxygen, nitrogen or sulfur;

$G^3$ for each occurrence is independently hydrogen or $(C_1-C_6)$alkyl;

$R^8$ for each occurrence is independently $(C_1-C_6)$alkyl or $(C_1-C_6)$alkoxy$(C_1-C_6)$alkyl;

$R^9$ and $R^1$ for each occurrence are independently hydrogen, $(C_1-C_6)$alkyl, $(C_3-C_8)$cycloalkyl, or $(C_1-C_6)$alkoxy$(C_1-C_6)$alkyl;

$R^{11}$ for each occurrence is independently hydrogen, $(C_1-C_6)$alkyl, $NR^9R^{10}$, $(C_3-C_8)$cycloalkyl, or $(C_1-C_6)$alkoxy$(C_1-C_6)$alkyl wherein $R^9$ and $R^{10}$ are as defined above;

m for each occurrence is independently an integer of 1 to 6; and n for each occurrence is independently 0 or an integer of 1 to 6;

with the provisos that:
(1) when $Q^9$ is O or S then n is not 0;
(2) when $Q^1$ is oxygen or sulfur then $Q^3$ is absent; and
(3) when $Q^2$ is nitrogen then $Q^5$ is absent.

A preferred process of the immediately foregoing process is a process wherein $R^1$ is —$NHCOCH_3$, —NHCO-t-Bu, —$NHCOCF_3$ or —NHCOO—$CH_2$-phenyl; and $R^2$ is hydrogen or methyl.

Another compound which is useful in the synthesis of a compound of formula (I) is a compound of the formula

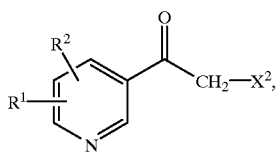

(a)

wherein
$R^1$ is selected from the group consisting of —$NR^3$—CO—$(C_1-C_{10})$alkyl, —$NR^3$—$CO_2$—$(C_1-C_{10})$alkyl, —$NR^3$—$CO_2$—$(CH_2)_a$-(optionally substituted phenyl), —$NR^3$—CO—$(CH_2)_a$-(optionally substituted phenyl), —$NR^3$—$SO_2$—$(C_1-C_{10})$alkyl, —$NR^3$—$SO_2$—$(CH_2)_a$-(optionally substituted phenyl) and —$NR^3$—CO—$(C_1-C_4)$ perfluoroalkyl;

$R^2$ is selected from the group consisting of hydrogen, amino, nitro, $(C_1-C_8)$alkylamino, fluoro, $CF_3$, $(C_1-C_4)$alkyl, $(C_1-C_4)$alkoxy, —$NR^3$—CO—$(C_1-C_{10})$alkyl, —$NR^3$—$CO_2$—$(C_1-C_{10})$alkyl, —$NR^3$—$CO_2$—$(CH_2)_a$-(optionally substituted phenyl), —$NR^3$—CO—$(CH_2)_a$-(optionally substituted phenyl), —$NR^3$—$SO_2$—$(C_1-C_{10})$alkyl, —$NR^3$—$SO_2$—$(CH_2)_a$-(optionally substituted phenyl) and —$NR^3$—CO—$(C_1-C_4)$perfluoroalkyl;

where a for each occurrence is independently 0, 1, 2, 3 or 4;

$R^3$ for each occurrence is independently selected from the group consisting of hydrogen and $(C_1-C_6)$alkyl; and optionally substituted phenyl group is optionally substituted with one, two or three substituents, each substituent is independently selected from the group consisting of hydroxy, fluoro, chloro, iodo, bromo, $CF_3$, sulfonamide, $(C_1-C_4)$alkyl, $(C_1-C_4)$alkoxy, carboxy, hydroxyalkyl, $(C_1-C_4)$alkoxycarbonyl, $(C_1-C_4)$thioalkyl, sulfonyl, sulfinyl and amino; and $X^2$ is Cl, Br or I.

A compound which is preferred among the immediately, foregoing group of compounds of formula (a) are those compounds wherein $R^1$ is —$NHCOCH_3$, —NHCO-t-Bu, —$NHCOCF_3$ or —NHCOO—$CH_2$-phenyl; and $R^2$ is hydrogen or methyl.

It will be appreciated by those skilled in the art that the compounds of formulas (I), (II), (III) and (Z*) may contain at least one chiral center. Accordingly, compounds of formulas (I), (II), (III) and (Z*) may exist in, and be isolated in, optically-active and racemic forms. Some compounds may exhibit polymorphism. It is to be understood that the present invention encompasses the racemic, optically-active, polymorphic and stereoisomeric forms, or mixtures thereof, it being well known in the art how to prepare optically-active forms. For example, by resolution of the racemic form by recrystallization techniques, by synthesis from optically-active starting materials, by chiral synthesis, or by chromatographic separation using a chiral stationary phase.

In this specification and the appendant claims the terms "alkyl" and "alkoxy" include both straight and branched chain radicals, but it is to be understood that references to individual radicals such as "propyl" or "propoxy" embrace only the straight chain ("normal") radical, branched chain isomers such as "isopropyl" or "isopropoxy" being referred to specifically.

DETAILED DESCRIPTION

In the discussion which follows, common chemical acronyms and abbreviations have been used: BOC (tertbutoxycarbonyl); CBZ (benzyloxycarbonyl); THF (tetrahydrofuran); DMF (dimethylformamide); NMP (N-methyl-2-pyrrolidinone); DMAC (N,N-dimethylacetamide); DME (dimethoxy-ethane); DMSO (dimethylsulfoxide); TFA (trifluoroacetic acid). "Lower" as; used herein (for example, when referring to a lower alkyl group or a lower alkanol) means a group having one to four carbon atoms.

The expression "reaction inert solvent" refers to any solvent or combination of solvents which does not interact with starting materials, reagents, intermediates or products in a manner which adversely affects the reaction or yield of the desired product.

A process for the manufacture of a compound of formula (I) as defined above is provided as a feature of the invention and is illustrated by the following procedure in which the meanings of generic radicals are as given above unless otherwise qualified. The process can be effected, generally as shown in Scheme 1.

Scheme 1

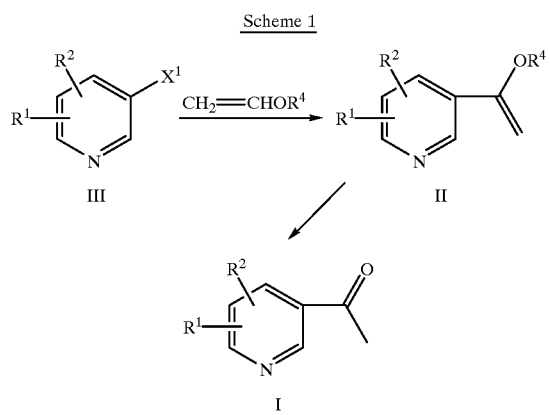

If they are not commercially available, the necessary starting materials for the following procedures may be made by standard organic chemical techniques known to those skilled in the art, techniques which are analogous to the synthesis of known compounds, or techniques which are analogous to the below described procedures or the procedures described in the examples.

A compound of formula (II) can be synthesized by treating a compound of formula (III) with a vinyl ether of the formula (IV), $CH_2$=$CHOR^4$, (where $R^1$, $R^4$ and $X^1$ are as previously defined) in the presence of a base, a phosphine and a palladium catalyst to afford a compound of formula (II). The reaction is typically implemented by stirring in a polar solvent such as an ether (e.g., THF, dioxane, DME), a lower trialkylamine, a polar aprotic solvent such as DMF, NMP, DMAC, or a mixture of these solvents, with acetonitrile being especially preferred. Suitable bases for the reaction include lower trialkylamines, sodium or potassium carbonate, or sodium or potassium bicarbonate, with trethylamine being particularly preferred. Suitable phosphines include triarylpihosphines such as triphenylphosphine and diphenyl-2-pyridylphosphine, with tri-ortho-tolylphosphine being especially preferred. The palladium catalyst may be selected from palladium on carbon or other solid support when $X^1$ is iodo, when $X^1$ is not iodo the palladium catalyst is selected from a variety of palladium salts and complexes, such as palladium (II) chloride, palladium (0) tetrakis (triphenyl-phosphine), palladium (II) bis (triphenylphosphine) chloride, palladium (0) bis (dibenzylidene-acetone), palladium (0) bis(benzonitrile), or allylpalladium chloride dimer, with palladium (II) acetate being especially preferred. The reaction is typically carried out at a temperature of about 20° C. to about 150° C., with a temperature of about 60° C. to about 110° C. being especially suitable.

A compound of formula (II) can be converted to a compound of formula (I) by treatment with an acid in the presence of water (the water may already be present in the acid in which case no additional water needs to be added). Prior isolation and/or purification of a compound of formula (II) is not generally required. Acids that may be used include sulfuric acid, phosphoric acid, perchloric acid, nitric acid, trichloroacetic acid, trifluoroacetic acid, oxalic acid, citric acid, methanesulfonic acid, sodium or potassium bisulfate, with hydrochloric acid being especially suitable. The reaction is typically implemented by stirring a compound of formula (II) with an acid in the presence of water, optionally in the presence of a polar co-solvent such as an ether, a lower alkyl alcohol, a lower alkyl ester, or a mixture of these solvents. The reaction is typically carried out at a temperature of about –20° C. to about 50° C.

Conventional methods and/or techniques of purification and separation known to those skilled in the art can be used to isolate the compounds of this invention. Such techniques include all types of chromatography (HPLC, column chromatography using common adsorbents such as silica gel, and thin layer chromatography), recrystallization, and differential (i.e., liquid-liquid) extraction techniques.

Acid addition salts of the compounds of the present invention may be useful in aiding in purifying said compounds as enabled by the disclosure herein. The acid addition salts of the compounds of the present invention are readily prepared by reacting the base forms with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However, when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

The compounds of formula (I) can be used to prepare β-adrenergic receptor agonists having the general formula (Z),

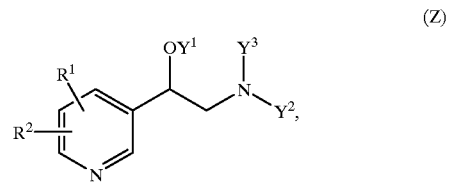

according to the following general procedure, where $R^1$ and $R^2$ are as defined herein for the compound of formula (I) and $Y^1$, $Y^2$ and $Y^3$ are any chemical substituents which can be attached to the atoms to which they are attached and confer β-adrenergic receptor activity, and as such have utility as hypoglycemic and antiobesity agents. Examples of such substituents and the resultant β-adrenergic receptor agonists can be found in PCT Publication No. WO 94/29290 published Dec. 22, 1994. Preferred embodiments of compounds of formula (Z) are compounds of formula (Z*),

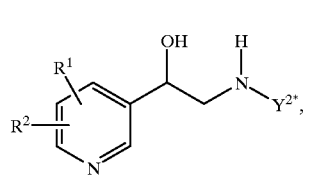

(Z*)

wherein $Y^1$ and $Y^3$ are each hydrogen and $Y^{2*}$ is as defined hereinabove.

The acetyl side chain of a compound of formula (I) is brominated with a bromine source, such as elemental bromine, phenyltrimethyl-ammonium tribromide or pyridinium hydrobromide perbromide and hydrogen bromide in acetic acid to prepare compound (a) where $X^2$ is Br. The reaction is complete in from 1 to 5 hours and is generally carried out at from about 0° C. to room temperature, with room temperature being preferred.

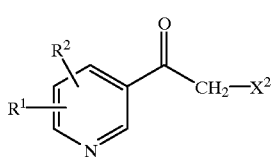

(a)

The reaction may also be carried out using the analogous chloro reagents to prepare compound (a) with a chloro substituted acetyl group, where $X^2$ is Cl. The acetyl side chain of a compound of formula (I) may be chlorinated with a chlorine source, such as chlorine gas dissolved in acetic acid, or trichloroisocyanuric acid and sulfuric acid in acetic acid, or chlorotrimethylsilane and dimethylsulfoxide in acetonitrile, to prepare compound (a) with a chloro substituted acetyl group, where $X^2$ is Cl. The acetyl side chain of a compound of formula (I) may also be iodinated with an iodine source, such as iodine and a soluble silver (I) salt, for example silver nitrate, in methanol, or N-iodosuccinimide in acetic acid, or potassium iodate and potassium iodide in sulfuric acid, to prepare compound (a) with an iodo substituted acetyl group, where $X^2$ is I. Compound (a) may be sequentially aminated and reduced to form compound (Z) or compound (a) may be reduced and treated with base to form an epoxide compound (c),

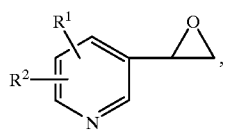

(c)

which is then aminated to also prepare compound (Z). The use of chiral reducing agents in this sequence allows the preparation of specific stereoisomers since the carbon atom bearing the hydroxy in compound (Z) is asymmetric.

In the reaction of compound (a) to prepare compound (Z) the starting material is placed in an aprotic solvent such as acetonitrile and excess amine (i.e., $HNY^2Y^3$, with $H_2NY^{2*}$ being the preferred amine and yielding a compound of formula (Z*)) and stirred for from about 10 minutes to 2 hours. The solvent is removed and the residue containing the aminated ketone intermediate of formula ($Z^1$), for example,

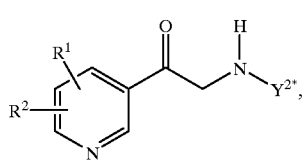

($Z^1$)

wherein $Y^{2*}$ is as defined hereinabove, which may be isolated but is usually not isolated, is dissolved in a protic solvent such as an alcohol and combined with a mild reducing agent preferably sodium borohydride at from about 0° to about 10° C. for from about 15 minutes to about 2 hours. The product is isolated using known techniques.

Compound (a) may also be converted into the epoxide (c) using a mild reducing agent such as sodium borohydride, lithium borohydride and the like. Such reducing agents will produce a racemic mixture of stereoisomers. Preferably a stereospecific reducing agent such as R-alpine borane may be used which will prepare the R-isomer of the epoxide substantially free of the S-isomer. The reaction is carried out in an inert solvent from 0° C. to room temperature, preferably at room temperature. The reaction is generally complete in from 1 to 10 days. The progress of the reaction is generally followed by taking aliquots of the reaction mixture and analyzing them for the presence of starting material using, for example, thin layer chromatography. Additional reducing agent may be added as needed. The reaction mixture is then treated with base, such as an alkali metal hydroxide, preferably sodium hydroxide in a protic solvent such as an alcohol or in the presence of a tertiary amine or with excess amine reactant (i.e., $HNY^2Y^3$, with $H_2NY^2$ being the preferred amine and yielding a compound of formula (Z*)). The reaction is generally complete in from about ½ to about 24 hours at from about 0° C. to room temperature, preferably room temperature.

The epoxide (c) is aminated using the excess amine reactant in an alcohol heated at from about 50° C. to reflux. The reaction is generally complete in from about 1 to about 24 hours. If compound (c) was prepared in a stereospecific manner the optical purity of the product, compound (Z), will be preserved.

The present invention is illustrated by the following Examples. However, it should be understood that the invention is not limited to the specific details of these examples.

EXAMPLE 1

N-(5-Acetyl-pyridin-2-yl)-acetamide

A mixture of 1.07 g (5 mmol) of N-(5-bromo-pyridin-2-yl)-acetamide, 1.00 g (10 mmol) of butyl vinyl ether, 0.245 g (0.8 mmol) of tri-o-tolylphosphine, 0.090 g (0.4 mmol) of palladium acetate, and 1.10 mL (7.9 mmol) of triethylamine in 10 mL of acetonitrile containing 15 mg of hydroquinone was heated at reflux for about 18 hours. The reaction mixture was then cooled, concentrated, and the residue was taken up in 10 mL of 6 M hydrochloric acid and stirred for about 15 minutes. The mixture was then diluted with 40 mL of ethyl acetate, adjusted to pH 8 with 6 M sodium hydroxide, and the aqueous phase was saturated with sodium chloride. The ethyl acetate layer was separated, dried, and concentrated. The residue was chromatographed on silica gel (2:1 ethyl acetate-hexanes), to afford 0.578 g of N-(5-acetyl-pyridin-2-yl)-acetamide as white needles, mp 146–147° C.

(recrystallization solvent=1:4 ethanol-hexanes); $^1$H nmr (deuteriochloroform): δ=8.82 (br s, 1 H), 8.21 (m, 3 H), 2.56 (s, 3 H), 2.22 (s, 3 H); ms (NH$_3$ Cl): m/z=179 (MH$^+$).

EXAMPLE 2

N-(5-Acetyl-pyridin-2-yl)-2,2-dimethyl-propionamide

A solution of 5.00 g (28.9 mmol) of 2-amino-5-bromopyridine in 20 mL of dichloromethane was treated sequentially with 3.50 g (34.6 mmol) of triethylamine followed by 3.50 g (29.2 mmol) of trimethylacetyl chloride. The reaction mixture was filtered after about 1 hour, and the filtrate was evaporated to a colorless oil. This was crystallized from hexanes, filtered and washed to afford 3.36 g of N-(5-bromo-pyridin-2-yl)-2,2-dimethyl-propionamide as white crystals, mp 57–59° C. $^1$H NMR (deuterochloroform) δ=8.28 (d, 1 H); 8.16 (d, 1 H); 7.96 (br, 1 H); 7.75 (d of d, 1 H); 1.29 (s, 9 H): MS (NH$_3$ Cl): m/z=257, 259 (M+H$^+$, Br isotopes).

Following the procedure of Example 1, the title compound was obtained from 3.84 g (15 mmol) of N-(5-bromo-pyridin-2-yl)-2,2-dimethyl-propionamide, 15 mL of acetonitrile, 3.15 mL (22.5 mmol) of triethylamine, 3.90 mL (30 mmol) of butyl vinyl ether, 135 mg (0.6 mmol) of palladium acetate, and 367 mg (1.2 mmol) of tri-o-tolylphosphine to afford 2.63 g of the title product as white rhombs after recrystallization of the crude product without chromatography, mp 113–115° C. (recrystallization solvent= 2-propanol); $^1$H nmr (deuteriochloroform): δ=8.84 (d, 1 H); 8.32 (d, 1 H); 8.23 (d of d, 1 H); 8.20 (br, 1 H); 2.59 (s, 3 H), 1.34 (s, 9 H); ms (NH$_3$ Cl): m/z=221 (MH$^+$).

EXAMPLE 3

N-(5-Acetyl-6-methyl-pyridin-2-yl)-acetamide

Following the procedure of Example 1, the title compound was obtained from 1.15 g (5 mmol) of N-(5-bromo-6-methyl-pyridin-2-yl)-acetamide, 10 mL of acetonitrile, 1.10 mL (7.5 mmol) of triethylamine, 1.00 g (10 mmol) of butyl vinyl ether, 90 mg (0.4 mmol) of palladium acetate and 245 mg 10.8 mmol) of tri-o-tolylphosphine to afford 0.92 g of the title product as white flakes after chromatography (2:1 hexanes-ethyl acetate), mp 201–202° C. (recrystallization solvent=2 propanol); $^1$H nmr (dimethylsulfoxide-d$_6$): δ=8.27 (d, 1 H), 8.01 (d, 1 H), 2.59 (s, 3 H), 2.53 (s, 3 H), 2.11 (s, 3 H); ms (NH$_3$ Cl): m/z=193 (MH$^+$).

EXAMPLE 4

N-(3-Acetyl-5-methyl-pyridin-2-yl)-acetamide

Following the procedure of Example 1, the title compound was obtained from 1.15 g (5 mmol) of N-(3-bromo-5-methyl-pyridin-2-yl)-acetamide, 10 mL of acetonitrile, 1.10 mL (7.5 mmol) of triethylamine, 1.00 g (10 mmol) of butyl vinyl ether, 90 mg (0.4 mmol) of palladium acetate, and 245 mg (0.8 mmol) of tri-o-tolylphosphine to afford 0.50 g of the title product as a white solid after chromatography (2:1 ethyl acetate-hexanes), mp 99–100° C.; (recrystallization solvent=2-propanol); $^1$H nmr (deuteriochloroform): δ=11.08 (br, 1 H), 8.41 (d, 1 H), 7.94 (d, 1 H), 2.63 (s, 3 H), 2.35 (s, 3 H), 2.34 (s, 3H); ms (NH$_3$ Cl): m/z=193 (MH$^+$).

EXAMPLE 5

N-(5-Acetyl-3-methyl-pyridin-2-yl)-acetamide

Following the procedure of Example 1, the title compound was obtained from 0.478 g (2.1 mmol) of N-(5-bromo-3-methyl-pyridin-2-yl)-acetamide, 5 mL of acetonitrile, 0.32 g (3.2 mmol) of triethylamine, 0.42 g (4.2 mmol) of butyl vinyl ether, 38 mg (0.17 mmol) of palladium acetate, and 103 mg (0.33 mmol) of tri-o-tolylphosphine to afford 0.162 g of the title product as a white solid after chromatography (2:1 ethyl acetate-hexanes), mp 115–116° C. (recrystallization solvent=ethyl acetate); $^1$H nmr (deuteriochloroform): δ=8.26 (d, 1 H), 7.79 (br, 1 H), 7.68 (d, 1 H), 2.24 (s, 9 H); ms (NH$_3$ Cl): m/z=193 (MH$^+$).

EXAMPLE 6

(5-Acetyl-pyridin-2-yl)-carbamic acid benzyl ester

Following the procedure of Example 1, the title compound was obtained from 1.50 g (5 mmol) of (5-bromo-pyridin-2-yl)-carbamic acid benzyl ester, 10 mL of acetonitrile, 1.10 mL (7.5 mmol) of triethylamine, 1.00 g (10 mmol) of butyl vinyl ether, 90 mg (0.4 mmol) of palladium acetate and 245 mg (0.8 mmol) of tri-o-tolylphosphine to afford 0.89 g of the title product as white needles after recrystallization of the crude product without chromatography, mp 186° C. (dec) (recrystallization solvent=ethyl acetate); $^1$H nmr (dimethylsulfoxide-d$_6$): δ=10.76 (br s, 1 H), 8.85 (d, 1 H), 8.25 (d of d, 1 H), 7.96 (d, 1 H), 7.41 (m, 5 H), 5.19 (s, 2 H), 2.54 (s, 3 H); ms (NH$_3$ Cl): m/z=271 (MH$^+$).

EXAMPLE 7

N-(5-Acetyl-pyridin-2-yl)-2,2,2-trifluoro-acetamide

Following the procedure of Example 1, the title compound was obtained from 1.34 g (5 mmol) of N-(5-bromo-pyridin-2-yl)-2,2,2-trifluoro-,acetamide, 10 mL of acetonitrile, 1.10 mL (7.5 mmol) of triethylamine, 1.00 g (10 mmol) of butyl vinyl ether, 90 mg (0.4 mmol) of palladium acetate, and 245 mg (0.8 mmol) of tri-o-tolylphosphine to afford 1.01 g of the title product as white needles after recrystallization of the crude product without chromatography, mp 147–149° C. (recrystallization solvent=ethyl acetate); $^1$H nmr (deuterio-chloroform): δ=8.35 (d, 1 H), 8.11 (d, 1 H), 7.91 (br, 1 H), 7.87 (d of d, 1 H), 2.35 (s, 3 H); ms (NH$_3$ Cl):m/z=233 (MH$^+$).

EXAMPLE 8

N-[5-(1-Butoxy-vinyl)-pyridin-2-yl]-acetamide

A mixture of 1.07 g (5 mmol) of N-(5-bromo-pyridin-2-yl)-acetamide, 1.00 g (10 mmol) of butyl vinyl ether, 0.245 g (0.8 mmol) of tri-o-tolylphosphine, 0.090 g (0.4 mmol) of palladium acetate, and 1.10 mL (7.9 mmol) of triethylamine in 10 mL of acetonitrile containing 15 mg of hydroquinone was heated at reflux for about 18 hours. The reaction mixture was then cooled, concentrated, and the residue was taken up in ether and water. The ether phase was separated, washed with water and brine, dried, and concentrated. The residue was chromatographed on silica gel (6:1 benzene-ethyl acetate) to afford 0.254 g of the title product as a colorless oil that rapidly crystallized, mp 55°–58° C. (recrystallization solvent=hexane). $^1$H nmr (deuteriochloroform): δ=8.48 (m, 1 H); 8.42 (br s, 1 H); 8.24 (m, 1 H); 7.93 (m, 1 H); 4.60 (d, 1 H); 4.23 (d, 1 H); 3.84 (t, 3 H); 2.21 (s, 3 H); 177 (m, 2 H); 1.48 (m, 2 H); 0.97 (t, 3 H). ms (EI): m/z=234 (M$^+$).

Preparation 1

N(5-Bromo-pyridin-2-yl)-acetamide

A solution of 25.0 g (144 mmol) of 2-amino-5-bromopyridine in 50 mL of acetic acid and 250 mL of acetic anhydride was heated at reflux for about 2 hours. The reaction mixture was then cooled and poured into 750 mL of water with stirring. After about 1 hour, the solution was adjusted to pH=10 with 50% sodium hydroxide solution and the precipitate was filtered, washed with water and dried to give 26.5 g of the title product as a white flaky solid, mp 175–176° C. $^1$H nmr (deuteriochloroform): δ=8.29 (d, 1 H); 8.12 (d, 1 H); 7.96 (br, 1 H); 7.78 (d of d, 1 H); 2.19 (s, 3 H). MS (El): m/z =214, 216 (M$^+$, Br isotopes).

Preparation 2

(5-Bromo-pyridin-2-yl)-carbamic acid benzyl ester

A solution of 2-amino-5-bromopyridine (6.92 g, 40 mmol) and 6.22 g (48 mmol) of diisopropylethylamine in 50 mL of chloroform was added dropwise to a solution of 8.19 g (48 mmol) of benzyl chloroformate in 20 mL of chloroform at about 0° C., with stirring. A voluminous white precipitate formed. After about 15 minutes, the mixture was filtered and the precipitate was washed three times with chloroform and dried to give 2.70 g of the title product, mp 184° C. (dec) (recrystallization solvent=2-propanol). $^1$H nmr (dimethylsulfoxide-d$_6$): δ=10.48 (br s, 1 H), 8.37 (d, 1 H), 7.98 (d of d, 1 H), 7.81 (d, 1 H), 7.40 (m, 5 H), 5.17 (s, 2 H); ms (NH$_3$ Cl): m/z=307, 309 (MH$^+$).

Preparation 3

N-(5-Bromo-pyridin-2-yl)-2,2,2-trifluoro-acetamide

Trifluoroacetic anhydride (4.20 g, 20 mmol) was added dropwise to a mixture of 3.46 g (20 mmol) of 2-amino-5-bromopyridine and 8.30 g (60 mmol) of powdered potassium carbonate in 25 mL of dichloromethane with stirring at about 0° C. After about 2 hours, the mixture was filtered, concentrated, and chromatographed (silica gel, 2:1 ethyl acetate-hexanes) to afford after concentration 1.50 g of the title product as white crystals, mp 70–72° C. (recrystallization solvent=2-propanol). $^1$H nmr (deuteriochloroform): δ=8.60 (br, 1 H), 8.39 (d, 1 H), 8.09 (d, 1 H), 7.88 (d of d, 1 H); ms (NH$_3$ Cl): m/z=269, 271 (MH$^+$).

Preparation 4

N-(5-Bromo-6-methyl-pyridin-2-yl)-acetamide

Following the procedure of Preparation 1, the title compound was obtained from 5.00 g (26.5 mmol) of 2-amino-5-bromo-6-methylpyrdine, 14 g of acetic anhydride and 14 mL of acetic acid to afford 4.70 g of the title product as white flakes, mp 156–157° C.; $^1$H nmr (deuteriochloroform): δ=8.11 (br, 1 H), 7.89 (d, 1 H), 7.74 (d, 1 H), 2.51 (s, 3 H), 2.16 (s, 3 H); ms (NH$_3$ Cl): m/z=229, 231 (MH$^+$).

Preparation 5

N-(3-Bromo-5-methyl-pyridin-2-yl)-acetamide

Following the procedure of Preparation 1, the title compound was obtained from 4.70 g (25.0 mmol) of 2-amino-3-bromo-5-methylpyridine, 12.8 g of acetic anhydride and 13 mL of acetic acid to afford 2.13 g of the title product as white needles, mp 65–66° C.; $^1$H nmr (deuteriochloroform): δ=8.34 (d, 1 H), 7.84 (d, 1 H), 2.42 (s, 3 H), 2.30 (s, 3 H); ms (NH$_3$ Cl): m/z=229, 231 (MH$^+$).

Preparation 6

N(5-Bromo-3-methyl-pyridin-2-yl)-acetamide

Following the procedure of Preparation 1, the title compound was obtained from 2.00 g (10.7 mmol) 2-amino-5-bromo-3-methylpyridine, 8 g of acetic anhydride and 8 mL of acetic acid to afford 1.71 g as a white solid, mp 109–110° C.; $^1$H nmr (deuteriochloroform): δ=8.47 (d, 1 H), 7.80 (d, 1 H), 2.25 (s, 3 H), 2.19 (s, 3 H); ms (NH$_3$ Cl): m/z=229, 231 (MH$^+$).

I claim:
1. A compound of formula (II),

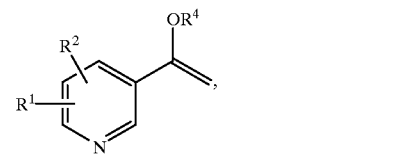

wherein
$R^1$ is selected from the group consisting of —NR$^3$—CO—(C$_1$–C$_{10}$)alkyl, —NR$^3$—CO$_2$—(C$_1$–C$_{10}$)alkyl, —NR$^3$—CO$_2$—(CH$_2$)$_a$-(optionally substituted phenyl), —NR$^3$—CO—(CH$_2$)$_a$-(optionally substituted phenyl), —NR$^3$—SO$_2$—(C$_1$–C$_{10}$)alkyl, —NR$^3$—SO$_2$—(CH$_2$)$_a$-(optionally substituted phenyl) and —NR$^3$—CO—(C$_1$–C$_4$)perfluoroalkyl;

$R^2$ is selected from the group consisting of hydrogen, amino, nitro, (C$_1$–C$_8$)alkylamino, fluoro, CF$_3$, (C$_1$–C$_4$)alkyl, (C$_1$–C$_4$)alkoxy, —NR$^3$—CO—(C$_1$–C$_{10}$)alkyl, —NR$^3$—CO$_2$—(C$_1$–C$_{10}$)alkyl, —NR$^3$—CO$_2$—(CH$_2$)$_a$-(optionally substituted phenyl), —NR$^3$—CO—(CH$_2$)$_a$-(optionally substituted phenyl), —NR$^3$—SO$_2$—(C$_1$–C$_{10}$)alkyl, —NR$^3$—SO$_2$—(CH$_2$)$_a$-(optionally substituted phenyl) and —NR$^3$—CO—(C$_1$–C$_4$)perfluoroalkyl;

where a for each occurrence is independently 0, 1, 2, 3 or 4;

$R^3$ for each occurrence is independently selected from the group consisting of hydrogen and (C$_1$–C$_6$)alkyl; and optionally substituted phenyl group is optionally substituted with one, two or three substituents, each substituent is independently selected from the group consisting of hydroxy, fluoro, chloro, iodo, bromo, CF$_3$, sulfonamide, (C$_1$–C$_4$)alkyl, (C$_1$–C$_4$)alkoxy, carboxy, hydroxyalkyl, (C$_1$–C$_4$)alkoxycarbonyl, (C$_1$–C$_4$)thioalkyl, sulfonyl, sulfinyl and amino; and $R^4$ is (C$_1$–C$_6$)alkyl.

* * * * *